US00PP24638P3

(12) United States Plant Patent
Brazelton et al.

(10) Patent No.: US PP24,638 P3
(45) Date of Patent: Jul. 15, 2014

(54) BLUEBERRY PLANT NAMED 'CLOCKWORK'

(50) Latin Name: *Vaccinium corymbosum*
Varietal Denomination: Clockwork

(75) Inventors: David M. Brazelton, Walterville, OR (US); Adam L. Wagner, Eugene, OR (US)

(73) Assignee: Fall Creek Farm and Nursery, Inc., Lowell, OR (US)

( * ) Notice: Subject to any disclaimer, the term of this patent is extended or adjusted under 35 U.S.C. 154(b) by 162 days.

(21) Appl. No.: 13/385,906

(22) Filed: Mar. 12, 2012

(65) Prior Publication Data

US 2013/0239264 P1 Sep. 12, 2013

(51) Int. Cl.
*A01H 5/00* (2006.01)

(52) U.S. Cl.
USPC ..... Plt./157

(58) Field of Classification Search
CPC ..... A01H 5/08
USPC ..... Plt./157
See application file for complete search history.

(56) References Cited

U.S. PATENT DOCUMENTS

PP6,700 P 3/1989 Wood

OTHER PUBLICATIONS

Pluto Upov Plant Variety Database 2013/03, retrieved on Sep. 25, 2013. Retrieved from the Internet at <http://www.upov.int/pluto/en/index.jsp> Citation for *Vaccinium* 'Clockwork', 3 pp.*

* cited by examiner

*Primary Examiner* — June Hwu
(74) *Attorney, Agent, or Firm* — Davis Wright Tremaine LLP; Dale C. Hunt; Wenhua Yu

(57) ABSTRACT

The new blueberry plant variety 'Clockwork' is provided. 'Clockwork' is a commercial variety with excellent machine harvest characteristics, and is intended for the processed foods market. The variety has a concentrated mid-season ripening schedule, with the potential to be harvested only once per season. 'Clockwork' holds up well in freezer trials, with excellent flavor and texture. The plant is vigorous, with an upright growth habit, and has an estimated chilling requirement of 800 to 1,000 hours.

3 Drawing Sheets

Latin name of the family, genus, and species: Family—Ericaceae. Genus—*Vaccinium*. Species—*corymbosum*.

Variety denomination The new blueberry plant claimed is of the variety denominated 'Clockwork'.

CROSS REFERENCE TO RELATED APPLICATIONS

None.

STATEMENT REGARDING FEDERALLY-SPONSORED RESEARCH AND DEVELOPMENT

None.

BACKGROUND OF THE INVENTION

The present invention relates to the discovery of a new and distinct cultivar of northern highbush blueberry known as a *Vaccinium corymbosum* referred to as 'Clockwork', as herein described and illustrated.

The new blueberry plant variety 'Clockwork' was selected in Lowell, Oreg. in 2005. 'Clockwork' is a commercial variety with excellent machine harvest characteristics, and is intended for the processed foods market. The variety has a concentrated mid-season ripening schedule, with the potential to be harvested only once per season. 'Clockwork' holds up well in freezer trials, with excellent flavor and texture. The plant is vigorous, with an upright growth habit, and has an estimated chilling requirement of 800 to 1,000 hours.

Pedigree and History: The new blueberry plant originated from a cross of 'Reka' (female parent, U.S. Plant Pat. No. 6,700, expired) by 'US645' (pollen parent, unpatented). The new blueberry plant variety 'Clockwork' has been planted in replicated trials since 2007.

The new variety can be compared to commercial variety 'Duke' in that 'Clockwork' ripens about 2 weeks later, has a smaller berry with a shallow calyx and has more concentrated ripening.

The new variety can be compared to commercial variety 'Draper' (U.S. Plant Pat. No. 15,103) in that 'Clockwork' has more concentrated ripening, a smaller berry with a shallow calyx, and a higher yield.

The new blueberry plant variety 'Clockwork' has maintained its distinguishing characteristics throughout successive asexual propagations. The variety has been repeatedly asexually reproduced through softwood cuttings in Lowell, Oreg., and the clones are phenotypically identical to the original plant.

SUMMARY OF THE INVENTION

The new blueberry plant variety 'Clockwork' has not been observed under all possible environmental conditions. The phenotype may vary somewhat with variations in environment and cultural practices such as temperature and light intensity without, however, any variance in genotype.

The following traits have been repeatedly observed in Lowell, Oreg., and are determined to be the unique characteristics of the new blueberry plant variety 'Clockwork':

1. Concentrated ripening schedule, with the potential to be harvested in one pick.
2. Excellent machine harvest characteristics, with a very upright growth habit and narrow crown
3. Medium sized berry with a very shallow calyx and excellent size and color uniformity

BRIEF DESCRIPTION OF THE DRAWINGS

The accompanying photographic illustration shows typical specimens in full color of the foliage and fruit of the new variety 'Clockwork'. The colors are as nearly true as is reasonably possible in a color representation of this type.

BOTANICAL DESCRIPTION

Figure 1:
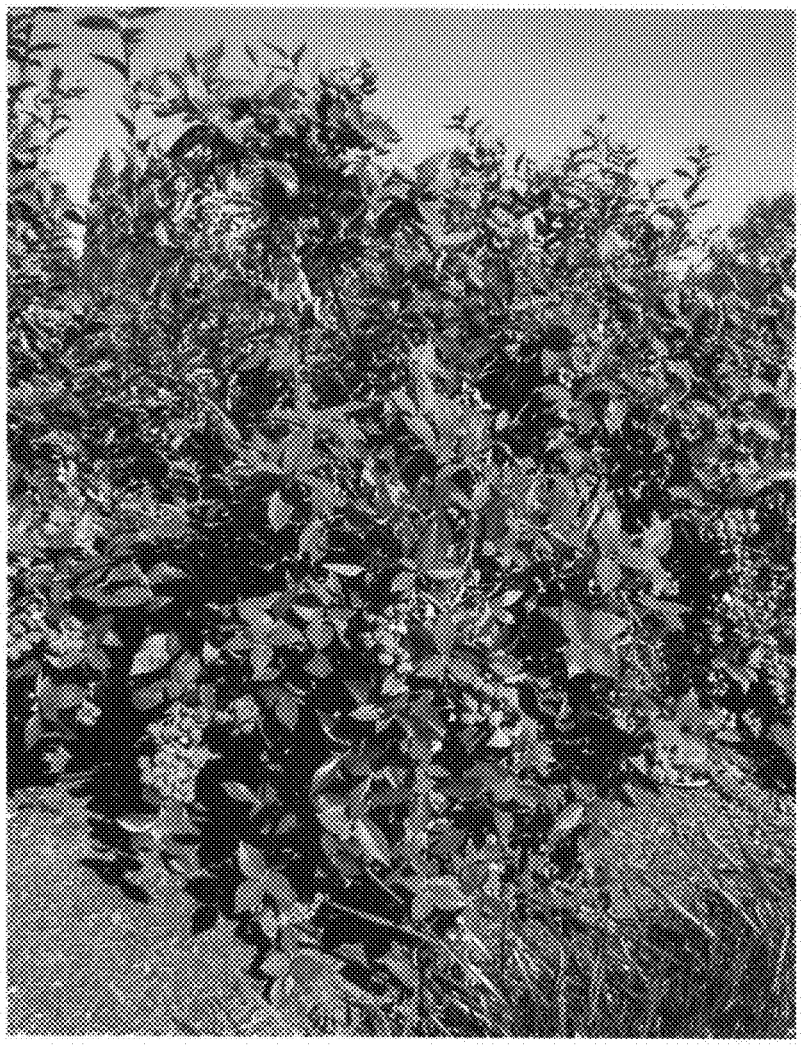
FIG. 1 is a photograph of the new variety 'Clockwork', highlighting the plant's upright growth habit and vigorous nature.
Figure 2:
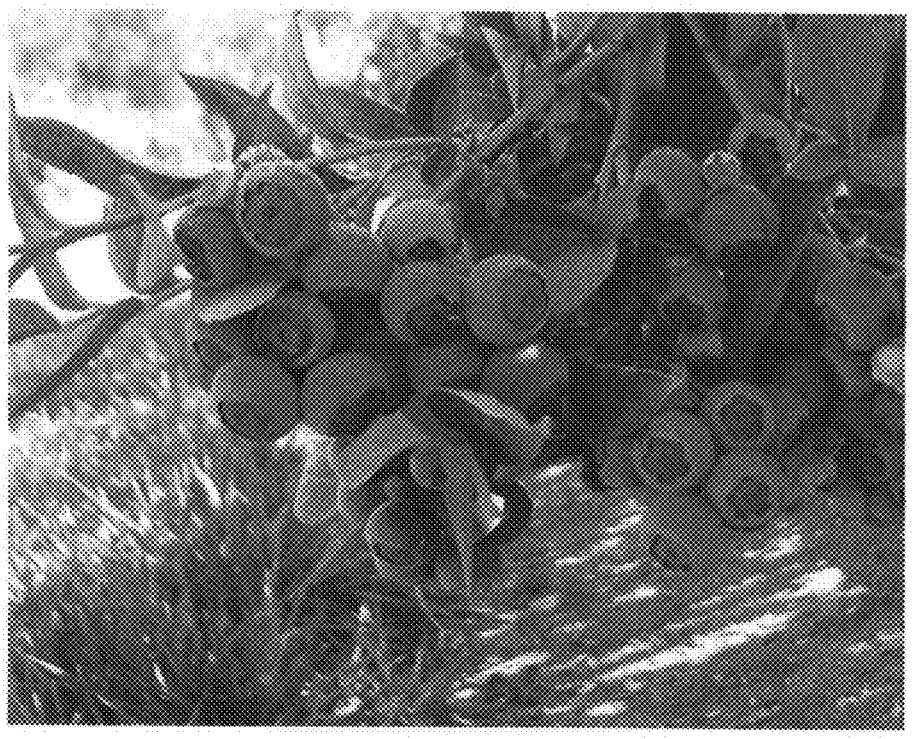
FIG. 2 is a photograph of the fruit of the new variety 'Clockwork'.
Figure 3:
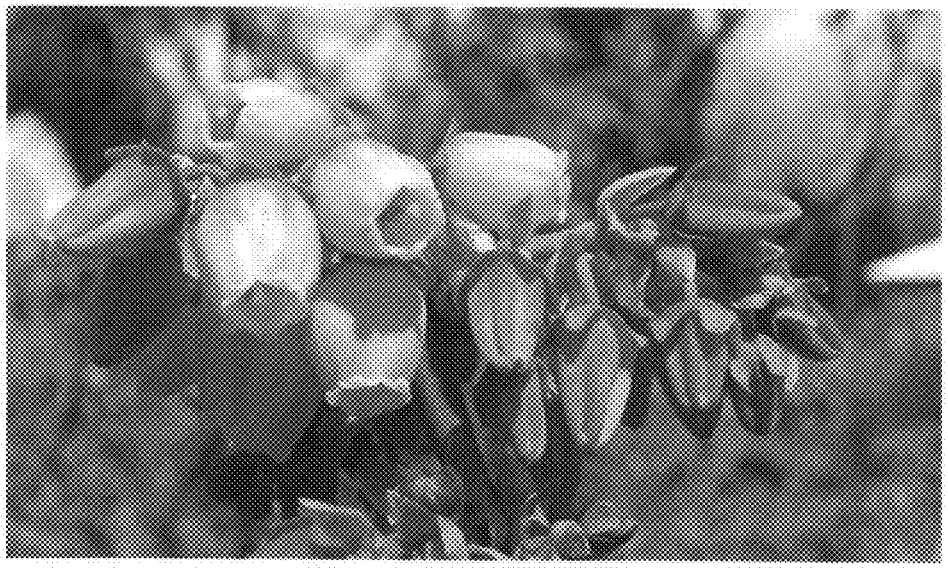
FIG. 3 is a photograph of the flowers of the new variety 'Clockwork'.

The following detailed description sets forth the distinctive characteristics of 'Clockwork'. The data which defines these characteristics was collected from asexual reproductions of the original selection. Dimensions, sizes, colors, and other characteristics are approximations and averages set forth as accurately as possible. The plant history was taken on plants approximately three years of age, and the descriptions relate to plants grown in the field in Lowell, Oreg. Color designations are from "The Pantone Book of Color" (by Leatrice Eiseman and Lawrence Herbert, Harry N. Abrams, Inc., Publishers, New York, 1990). Where the Pantone color designations differ from the colors in the photographs, the Pantone colors are accurate.

Classification:

*a. Family.*—Ericaceae.
*b. Genus.*—*Vaccinium.*
*c. Species.*—*corymbosum.*
*d. Common name.*—Highbush Blueberry.

Parentage:

*Female parent.*—'Reka' (U.S. Plant Pat. No. 6,700, expired).
*Male parent.*—'US645' (unpatented).

Market class: 'Clockwork' is a commercial blueberry variety intended to be machine harvested for the processed foods market.

PLANT

Plant size:

*a. Height of plant.*—Average of 35 inches on 4 year old plants.
*b. Canopy diameter.*—Average of 35 inches on 4 year old plants.

Growth habit: Upright.
Plant vigor: Vigorous.
Twigginess: Moderately twiggy.
Suckering: Low.
Evergreenness: Deciduous.
Chilling requirement: Approximately 800-1000 hours.
Cold hardiness: Approximately USDA zones 4-7.
Productivity in Lowell, Oreg:

*a. On* 2 *year old plants.*—Approximately 2.17 lbs per plant, compared to 1.55 lbs per plant on Draper plants of the same age.
*b. On* 3 *year old plants.*—Approximately 5.26 lbs per plant, compared to 3.96 lbs per plant on Draper plants of the same age.
*c. On* 4 *year old plants.*—Approximately 9 lbs per plant, compared to 7.77 lbs per plant on Draper plants of the same age.

Propagation: Easy to propagate from softwood cuttings.
Disease and pest resistance/susceptibility:

*a. Root rot* (*Phytophthora cinnamomi*).—Does not appear to be overly susceptible.
*b. Stem blight* (*Botryosphaeria* spp).—Undetermined.
*c. Botryosphaeria stem canker* (*Botryosphaeria* spp).—Undetermined.
d. *Phomopsis twig blight* (*Phomopsis vaccinii*).—Does not appear to be overly susceptible.
*e. Bacterial cane canker* (*Pseudomonas syringae*).—Does not appear to be overly susceptible.
*f. Botrytis blight* (*Botrytis cinerea*).—Does not appear to be overly susceptible.
*g. Leaf spot* (*Septoria* spp.).—Does not appear to be overly susceptible.
*h. Leaf rust* (*Naohidemyces vaccinii*).—Does not appear to be overly susceptible.
*i. Bud mites* (*Acalatus vaccinii*).—Undetermined.

Disease survival: Good.

TRUNK AND BRANCHES

Texture:

*a. Surface texture new wood.*—Smooth.
*b. Surface texture* 1 *yr wood.*—Smooth.
*c. Surface texture* 3 *yr wood.*—Rough.

Color:

*a. Color of new wood.*—Pantone color Green Olive 17-0535.
*b. Color of rough bark at* 1 *year.*—Pantone colors Green Oasis 15-0538 and Red Barn Red 18-1531.
*c. Color of rough bark at* 3 *years.*—Pantone colors Ecru Drab 14-1212, Brown Sugar 17-1134, and Red Barn 18-1531.

FOLIAGE

Internode length: Average of 13.85 mm.
Leaf dimensions:

*a. Leaf length.*—Average of 69.6 mm.
*b. Leaf width.*—Average of 33.4 mm.

Leaf shape: Elliptical with acute apex and rounded base.
Leaf margin: Entire.
Leaf color:

*a. Upper leaf surface.*—Pantone color Black Forest 19-0315.
*b. Lower leaf surface.*—Pantone color Water Cress 17-0220.

Fall foliage color: Pantone Crushed Berry 18-1418.
Pubescence:

*a. Upper leaf surface.*—Absent.
*b. Lower leaf surface.*—Absent.
*c. Leaf margins.*—Absent.

Petiole:

*a. Petiole length.*—Average of 2.3 mm.

*b. Petiole color.*—Pantone color Celery Green 13-0532.

*c. Petiole surface texture.*—Smooth.

Leafing vs flowering: In Lowell, Oreg. flower bud break occurs prior to vegetative bud break. Flowers persist during initial vegetative growth period.

FLOWERS

Flower arrangement: Flowers arranged alternately on terminal end of branches.

Fragrance: Sweet, faint.

Immature flower color: Pantone colors Claret Red 17-1740 and Snow White 11-0602.

Flower buds: Loose cluster, moderate density.

Flower shape: Urceolate to cylindrical.

Flowering cluster: Loose.

Flowering period: 50% bloom occurs in the first week of May in Lowell, Oreg. and flowering continues through the end of May, compared to 'Duke' which blooms about one week earlier.

Number flowers: Average 7-8 flowers per cluster.

Pollen:

*a. Pollen staining.*—Approximately 90% viable, staining with 2% acetocarmine dye.

*b. Pollen abundance.*—Medium.

*c. Pollen color.*—Pantone color Corn Silk 13-0932.

Flower length: Average of 9.85 mm.

Corolla:

*a. Corolla length.*—Average of 8.07 mm.

*b. Corolla diameter.*—Average of 7.63 mm.

*c. Corolla aperture.*—Wide, average of 4.60 mm.

*d. Corolla color.*—Pantone color Snow White 11-0602.

*e. Corolla texture.*—Smooth.

Style length: Average of 6.91 mm.

Calyx:

*a. Calyx diameter.*—Average of 7.40 mm.

*b. Calyx surface.*—Smooth.

*c. Calyx color.*—Pantone color Water Cress 17-0220, lobes Herbal Garden 15-0336 and Holly Berry 17-1633.

Pistil color: Pantone color Green Oasis 15-0538.

Pedicel:

*a. Pedicel length flower.*—Average of 6.24 mm.

*b. Pedicel color.*—Pantone color Spinach Green 16-0439, Wild Rose 16-1715, and Rapture Rose 17-1929.

Peduncle:

*a. Peduncle length flower.*—Average of 14.98 mm.

*b. Peduncle color.*—Pantone color Mellow Green 12-0426 and Red Earth 18-1444.

Anther:

*a. Anther length.*—Average of 3.91 mm.

*b. Anther color.*—Pantone color Gold Earth 15-1234.

Stigma location: Stigma is even with lip of corolla and up to 0.17 mm above lip of corolla, on average.

Self-compatibility: Moderate — average of 56% of self-pollinated flowers reached maturity (cross-compatibility trials were completed on field plants, and may not represent accurate self-compatibility. Trials to be carried out again in 2012).

Updated self compatibility: Self Compatibility in 2012 greenhouse trials was good — 63 out of 66 (95%) flowers pollinated produced mature fruit.

Average inflorescence size: 31.07 mm.

FRUIT

Mean harvest date: July 23.

Mean date last pick: July 30.

Calyx:

*a. Calyx aperture.*—Average 9.7 mm.

*b. Calyx lobes.*—5 lobes, not well defined.

*c. Calyx depth.*—Average of 0.29 mm, noticeably shallow.

Berry cluster: Loose.

Berries per cluster: Average of 7-8.

Berry pedicel:

*a. Length.*—Average of 9.6 mm.

*b. Surface texture.*—Smooth.

Berry peduncle:

*a. Length.*—Average 24.2 mm.

*b. Surface texture.*—Smooth.

Berry detachment: Easy.

Berry weight: Average berry weight of 1.6 g, compared to Draper plants of the same age, which have an average berry weight of 2.0 g.

Berry height: Average of 12.1 mm.

Berry width: Average of 15.1 mm.

Berry shape: Oblate.

Berry color:

*a. Immature berry color.*—Pantone color Oasis 16-0540.

*b. Berry skin color on plant.*—Pantone color Blue Ice 17-3922.

*c. Berry skin color after harvest.*—Pantone color Velvet Morning 18-3927.

*d. Berry skin color after polishing.*—Pantone color Dark Navy 19-4013.

Berry wax: Medium wax, moderately persistent.

Berry flesh color: Pantone color Willow Green 15-0525.

Pedicel scar: Average 2.6 mm in diameter, small and dry.

Berry firmness: Firm. Average berry firmness of 208.75 g/mm of deflection, compared with Draper plants harvested on the same day, which had an average berry firmness of 223.29 g/mm of deflection, as measured with a Firmtech fruit firmness tester.

Berry flavor: Complex, fruity flavor.

Berry texture: Firm.

SEEDS

Seed color: Pantone color Rawhide 18-1137.

Seed length: Average of 1.46 mm.

Seed width: Average of 0.83 mm.

Seed weight: Average 0.3 mg.

Quantity seeds per berry: Average of 30 seeds per berry.

TABLE 1

| DISTINGUISHING FEATURES FROM PARENTS | | | |
|---|---|---|---|
| Name of parent | Characteristic(s) in which the candidate variety differs from the parent | Describe the expression of the characteristic for the parent | Describe the expression of the characteristic for 'Clockwork' |
| US645 | Depth of calyx basin | medium | Shallow or protruding (convex) |
| US645 | Fruit shape in longitudinal section | Round | oblate |

TABLE 1-continued

| DISTINGUISHING FEATURES FROM PARENTS | | | |
|---|---|---|---|
| Name of parent | Characteristic(s) in which the candidate variety differs from the parent | Describe the expression of the characteristic for the parent | Describe the expression of the characteristic for 'Clockwork' |
| Reka | Stem pubescence | Pubescent | Non-pubescent |
| Reka | Time of fruit ripening (1 year old shoots) | Early | Medium |

The invention claimed is:

1. A new and distinct variety of blueberry plant named 'Clockwork', substantially as illustrated and described herein.

* * * * *